United States Patent [19]
May

[11] Patent Number: 6,007,582
[45] Date of Patent: Dec. 28, 1999

[54] PROSTHETIC FOOT WITH MEANS FOR ENERGY STORAGE AND RELEASE

[75] Inventor: Denis Ronald William May, Esher, United Kingdom

[73] Assignee: Ortho Europe Limited, Abingdon Science Park

[21] Appl. No.: 08/900,628

[22] Filed: Jul. 25, 1997

[51] Int. Cl.⁶ ........................................ A61F 2/66
[52] U.S. Cl. .............................. 623/55; 623/56
[58] Field of Search .......................... 623/53–56

[56] References Cited

U.S. PATENT DOCUMENTS

| | | | |
|---|---|---|---|
| 3,551,914 | 1/1971 | Woodall | 623/53 |
| 4,364,128 | 12/1982 | Mummert | 623/53 |

FOREIGN PATENT DOCUMENTS

| | | | |
|---|---|---|---|
| 165570 | 3/1950 | Austria | 623/53 |
| 489 239 | 1/1919 | France . | |
| 22533 | 7/1921 | France | 623/53 |
| 25322 | 1/1923 | France | 623/53 |
| 309 066 | 11/1918 | Germany . | |
| 628958 | 9/1949 | United Kingdom | 623/53 |
| 1 134 045 | 11/1968 | United Kingdom . | |
| WO92/20305 | 11/1992 | WIPO . | |

*Primary Examiner*—David H. Willse
*Attorney, Agent, or Firm*—Dorn, McEachran, Jambor & Keating

[57] ABSTRACT

A prosthetic foot (10) comprising a movable heel mechanism (12), an energy storing device (14) acted on by to the movable heel mechanism (12) to store energy, and a control device (16) attached to the energy storage device (14) and to a release device which enables the stored energy to be released to provide a lift-off force in push-off.

9 Claims, 5 Drawing Sheets

FIGURE 1 TYPICAL READOUT OF NORMAL WALKING

FIGURE 2 TYPICAL READOUT OF ACTIVE AMPUTEE

PROSTHETIC FOOT WITH MEANS FOR ENERGY STORAGE AND RELEASE

The present invention relates to a prosthetic foot for use by amputees.

The design of such a prosthetic foot including an ankle presents some of the most difficult problems in the field of prosthetics from the engineering point of view.

The very large forces and moments which are generated about the ankle when walking, running or jumping dictate that such a foot must be very robust and strong. On the other hand it is the farthest point from an articulating knee axis and thus its weight has great influence on the inertia of the shank, and must therefore be kept to an absolute minimum. Indeed, the strength to weight requirements of prosthetic devices are more onerous than those of aerospace structures and aeronautics.

Upon heel contact immediately after the swing phase of walking, controlled plantar flexion, inversion/eversion and polar rotation of the ankle is required such that the foot accommodates to the terrain and cushions the impact shock. This must be accomplished silently and smoothly without transmitting undue suddenly applied loads to the amputee. After heel contact the joint should lock sufficiently to impart stability, but not such that dorsiflexion is inhibited and give a smooth progression into the roll-over phase. This is the phase where the whole of the body of the amputee is instantaneously revolving about the prosthetic ankle and the contralateral leg is swinging through. The controlled dorsiflexion of the ankle is required during the roll-over phase possibly coupled with some knee flexion/extension such that pelvic lift is minimised.

In the last part of the roll-over phase controlled flexion of the metatarsal phalangeal joint (the toe joint) should ensue to store some energy for the push-off phase. Immediately prior to the push-off phase plantar flexion of the ankle and extension of the knee and toe joint should begin to inhibit pelvic drop and give smooth transition for the push-off phase. At push-off the energy stored by dorsiflexion of the ankle and flexion of the toe joint should be smoothly dissipated to initiate the swing phase on the prosthetic side.

Ideally, during the swing phase the ankle should dorsiflex and thus permit the toe to clear the ground and swing through. Finally, at the end of the swing phase the foot should be re-positioned again ready for the next heel contact.

For an ideal prosthetic foot, to function in the above described manner, the stiffness of the various movements and the maximum moments and torques need to be carefully analysed. The foot should be able to plantarflex through about 15°. The stiffness required is of the order of about 1.13 newton meters per degree, thus achieving a maximum torque output of about 17 newton meters. Ideally, the dorsiflexion control should be highly non-linear with stiffness of about 4 newton meters per degree at 7°, rising through 6 newton meters per degree at 9°, to a maximum torque of about 40 newton meters in excess of 12° of movement. Inversion/eversion of the foot is often omitted in ankle designs, but when this is incorporated an angular movement of about ±18° is desirable. Again, with a stiffness of about 1.2 newton meters per degree, resulting in a torque output of ±20 newton meters.

Internal/external rotation that is polar rotation about the axis of the leg, again, is often omitted, or it may be incorporated away from the ankle joint in a separate rotator. A maximum movement of about ±7° is usually sufficient with a stiffness of approximately 1.7–2.3 newton meters per degree.

The toe joint should accommodate up to about 12° of flexion and, again, the stiffness should be non-linear about 1.6 newton meters per degree at 10° and rising to a maximum torque output of about 34 newton meters at 12°.

The above data quoted is for the ideal function of a foot for the average European male weighing some 90 kg, and stiffness, of course, should be adjusted for small men/ladies at one end and very heavy amputees at the other end of the scale. There are already a very large number of prosthetic feet and ankle joints available on the market today, these include, simple Sach type feet, Multi Flex Ankle, conventional Uniaxial Ankle and Foot, and newer devices such as the Quantum Foot, True Step and Master Step which go some way to mimicking the idealised function of the foot. Very expensive carbon fibre moulded construction feet which store energy in the whole of the structure of the lower limb, such as Flex Walk and Spring Lite still do not give ideal functions particularly in push-off support. Many of the feet available on the market have been studied using advanced clinical gait analysis techniques, FIG. 1 shows a typical graph of the ground reaction force for a normal person walking, showing the classical two-peak characteristic curves. For normal walking this first peak a is about 1.27×the body weight of the patient, and occurs at about 20% of the stance phase. This is followed by a minimum peak b which is in the order of about 60% of the body weight. During the latter stages of the stance phase just before toe-off, a second peak c occurs which is usually in the order of about 1.1 body weight and occurs at about 75% of the stance phase.

FIG. 2 shows a typical readout from an active amputee, who would be classed in mobility grading as 'Grade 6', in other words, a normal and a good walker. From this Figure it can be seen that the initial loading accommodation of most of the prosthetic feet today in the first peak d is adequate and approaches that required for the normal ideal foot. However the loss of support function just prior to push-off is evident from the lower second peak e in the graph, and it can be seen that all the feet, even the expensive so-called energy storing devices are significantly letting the patient down in their poor performance at push-off. Passive devices available on the market cannot compete with normal active dorsiflexion/plantar flexion of the ankle in this phase.

The aim of the present invention is to provide a remedy.

The present invention is directed to a prosthetic foot comprising a movable heel mechanism, an energy storing means acted on by the movable heel mechanism to store energy, and a control device attached to the energy storage means and to a release device which enables the stored energy to be released to provide a lift-off force in push-off.

Preferably the foot further comprises a toe spring which acts as the release device.

Advantageously the energy release takes place at a specific event during the gait cycle.

In a preferred embodiment the control device controls the release of the energy by the energy storage means such that it is dependent a upon one or more gait cycle variables.

Advantageously the control device can be externally adjusted.

Preferably the control device controls the rate of release of the energy by external adjustment.

In a preferred embodiment the control device is an automatic clevis type locking mechanism.

Preferably the control device is a cam device operated by a servo-electric motor controlled by computer.

Advantageously, the energy storage means is an elastomer or rubber buffer, a gas filled strut, a metal or composite spring, or hydraulic or pneumatic cylinder.

The present invention provides the advantage of collecting the energy associated with heel loading under the first peak d in FIG. 2, store it for a few milliseconds during the mid-stance and roll-over phase, and then release the energy to augment the second peak e in FIG. 2 just prior to push-off.

FIG. 3 is a graph which shows the energy storage areas in a ground reaction force curve and it can be seen that at heel contact about three times the energy that is required for push-off can be stored to enable normal active push-off. This 30% efficiency is equivalent to the theoretical thermodynamic efficiency of the Carnot cycle. In simple mechanical devices such as a foot according to the present invention the efficiencies may be better than 30%, with losses being mainly due to friction in the locks and pivots, strain energy losses in the springs and hysteresis and heating losses in the compliant energy storage devices. Nevertheless, there should, however, be plenty of energy reserve for significant active improved push-off.

A prosthetic foot made in accordance with the present invention will now be described with reference to FIGS. 4 and 5 of the attached drawings, in which:

BRIEF DESCRIPTION OF THE DRAWINGS

FIG. 4 shows a prosthetic foot 10 which fits the normal structural and functional requirements of any prosthetic foot and ankle device. The prosthetic foot 10 comprises a heel loading mechanism 12, a compressible energy storing means 14 with a locking mechanism 16 and a toe spring 18 connected to the locking mechanism 16 by an adjustable connecting rod 44.

Figure 1:
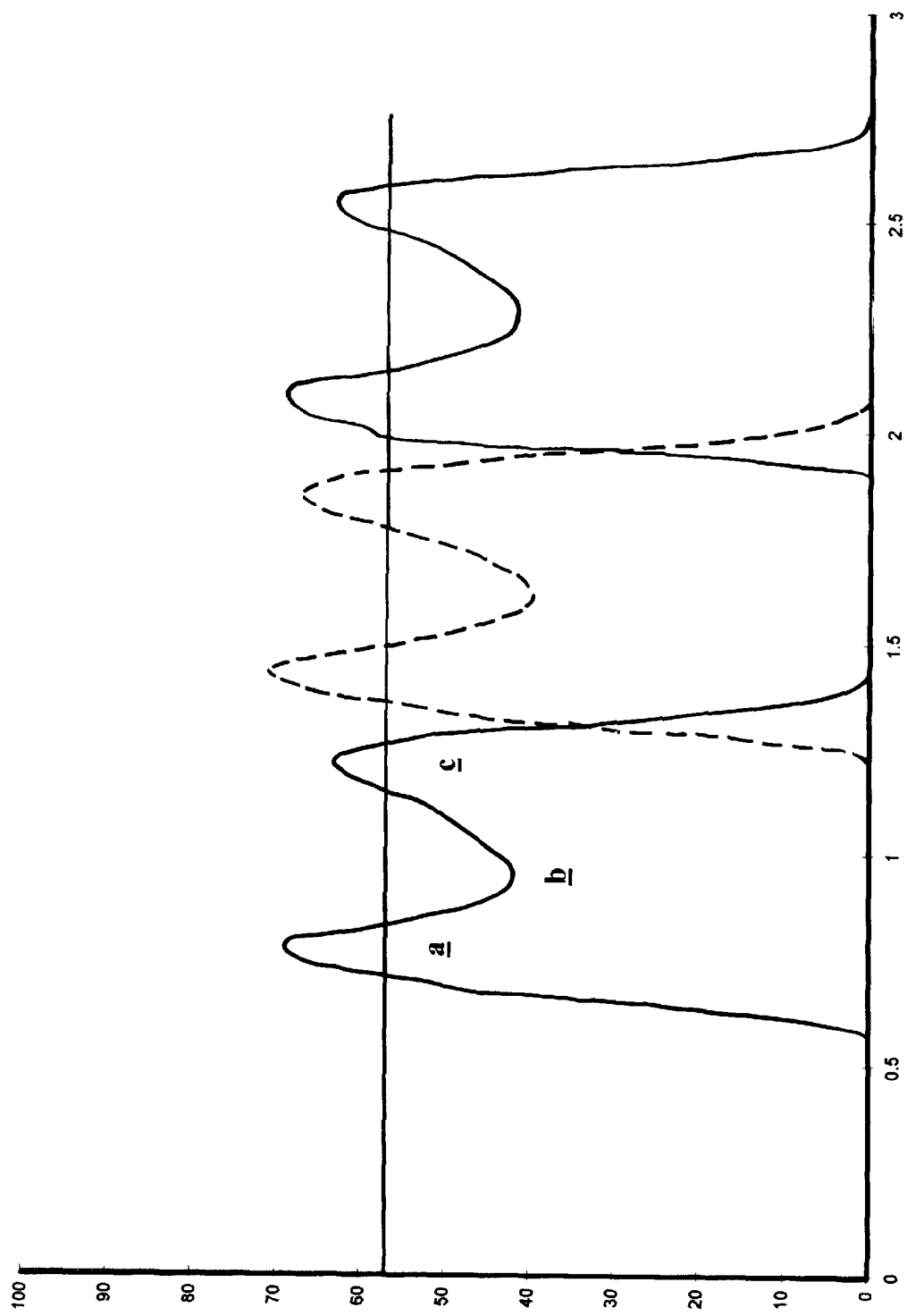
FIG. 1 is a typical readout of normal walking with the Y axis representing values of body weight and the X axis representing time.
Figure 2:
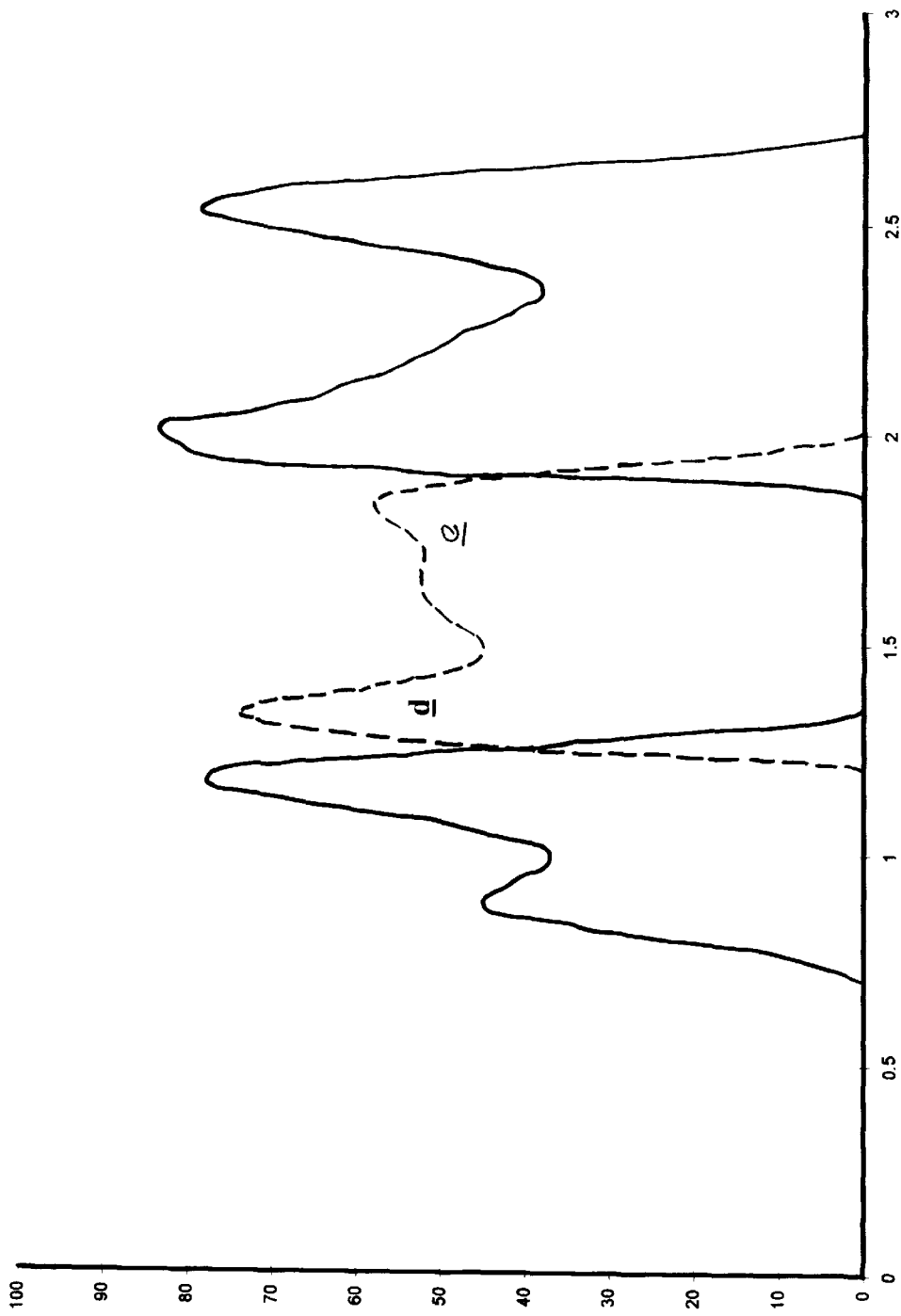
FIG. 2 is a typical readout of walking by an active amputee with the Y axis representing values of body weight and the X axis representing time.
Figure 3:
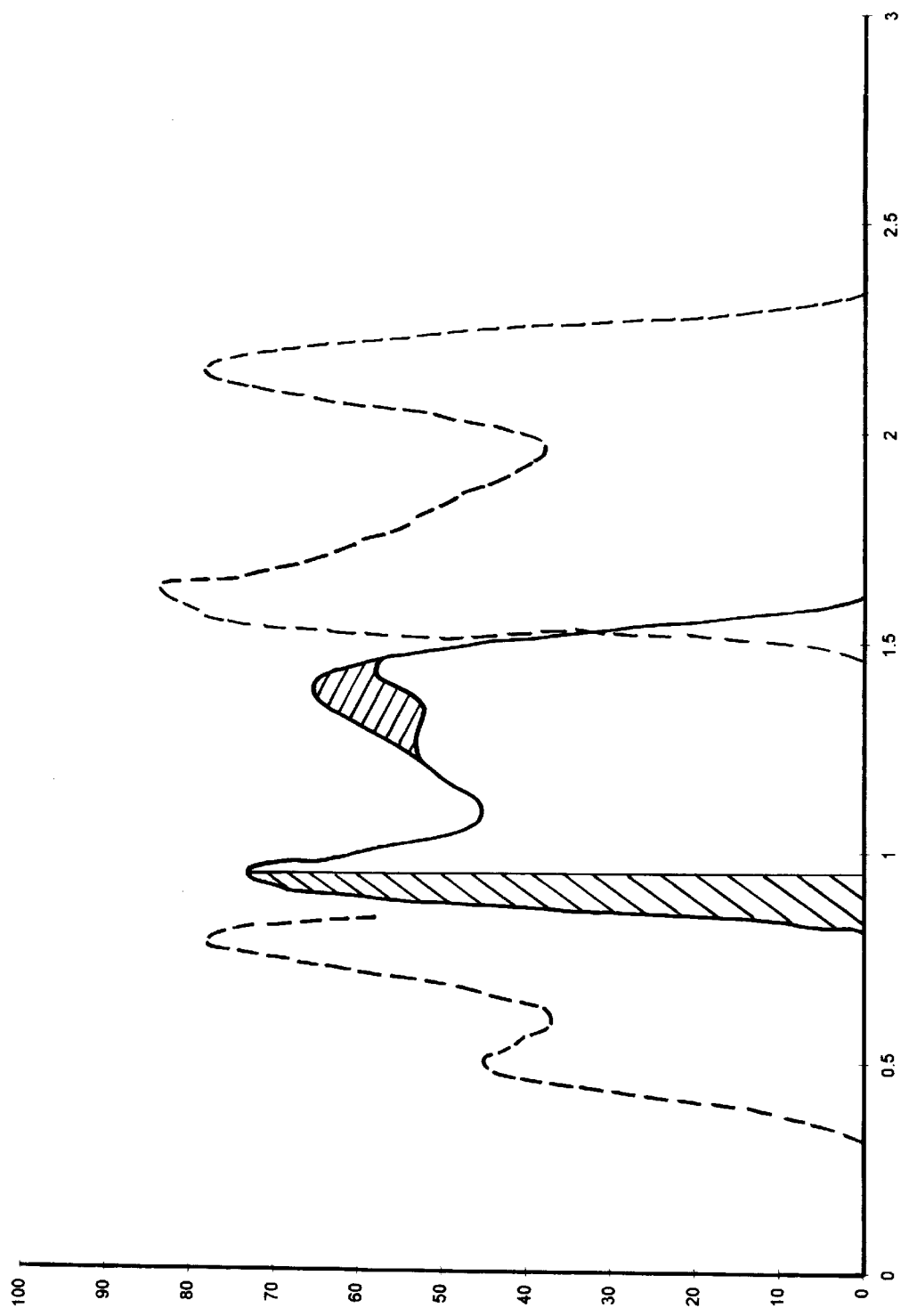
FIG. 3 illustrates the typical theoretical energy storage and recovery areas in walking, with the Y axis representing values of body weight and the X axis representing time.
Figure 4:
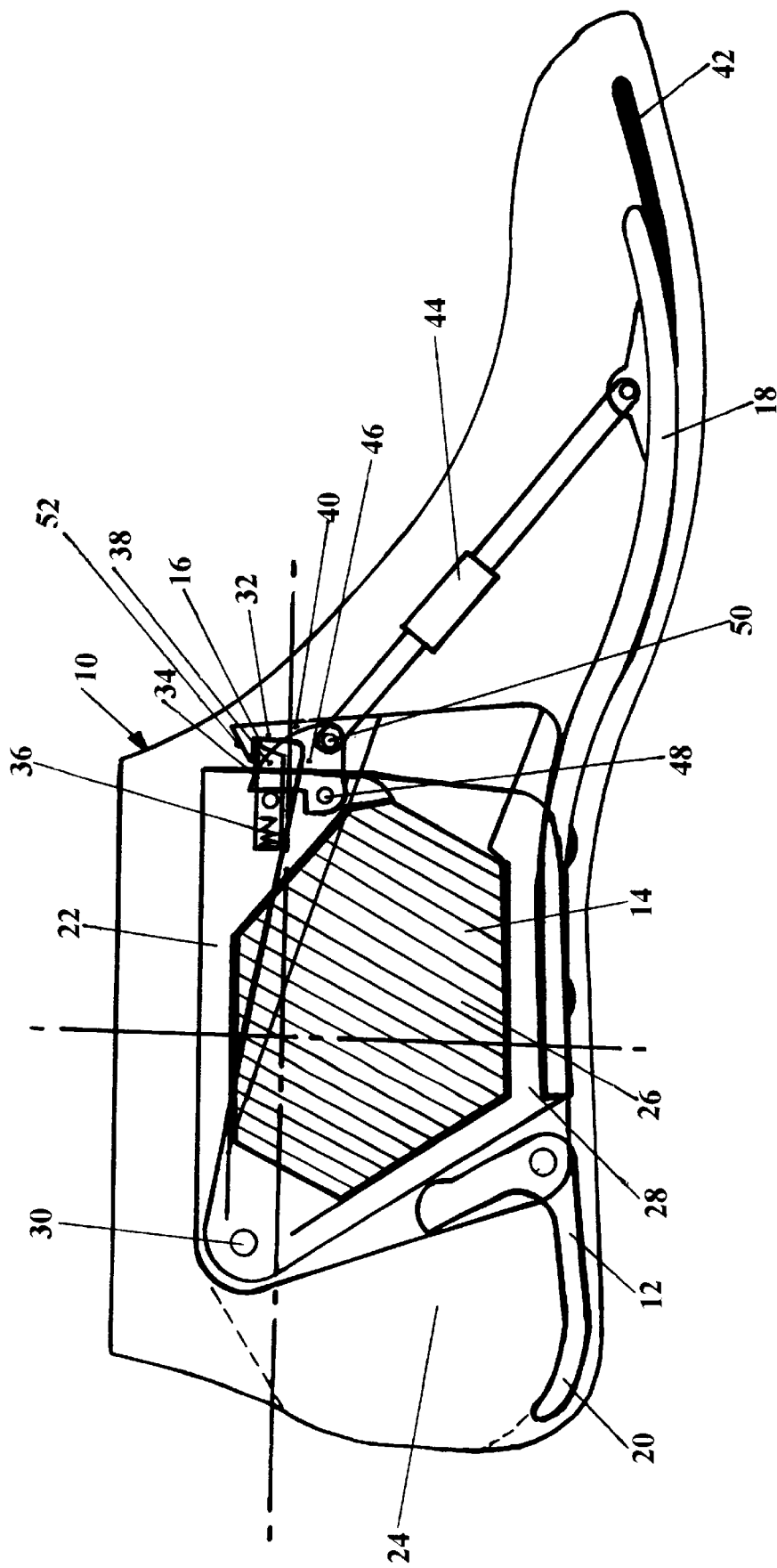
FIG. 4 is a sectional view of such a prosthetic foot.

The heel loading mechanism 12 comprises a lever 20 which has a L-shape The lever 20 is pivotably attached by the corner of the L to a chassis 22 of the prosthetic foot 10. One side of the L of the lever 20 projects along the base of the foot 10 while the other side of the L contacts the energy storage mechanism 14. Between the heel loading lever 20 and the chassis 22 of the foot 10 there is a heel cushion 24. The chassis 22 of the prosthetic foot 10 contains the energy storage means 14. The energy storage means comprise for instance an elastomer or rubber buffer 26 held within the chassis 22 There is a storage lever 28 between the elastomer or rubber buffer 26 and the heel loading lever 20, which is pivotally attached to a top part of the chassis 22 via a pivot 30. The storage lever 28 has a substantially elongated U-shape with the pivot 30 being at the top of the rearward arm of the U. At the top of the forward arm of the U of the storage lever 28 there is an inward facing cut-out 32. The cut-out 32 forms part of the locking mechanism 16 which is in the form of a spring assisted automatic clevis type lock. There is a slot 34 cut in the chassis 22 which contains a coil spring 36 which rests at one end on the chassis 22 and at the other upon a latch 38 which has a protrusion 40 extending beyond the side of the chassis 22. When extended by the spring 36 the latch 38 can engage the cut-out 32. The toe-spring 1B is fixedly attached to the bottom of the chassis 22 and has some degree of resilience. The toe-spring 18 is equipped at its toe end with a balata protector 42. An adjustable rod 44 is pivotally connected to the toe-spring 18 close to its toe end. The other end of the adjustable rod 44 is pivotally attached to a latch release cam 46. The latch release cam 46 is pivotally attached to the chassis 22. The latch release cam 46 has a somewhat triangular shape with at one corner a pivot 48 by which it is attached to the chassis 22, at another corner a pivot 50 by which it is attached to the adjustable connecting rod 44 and at the other corner there is a surface which abuts the protrusion 40 of the spring loaded latch 3B.

Figure 5:
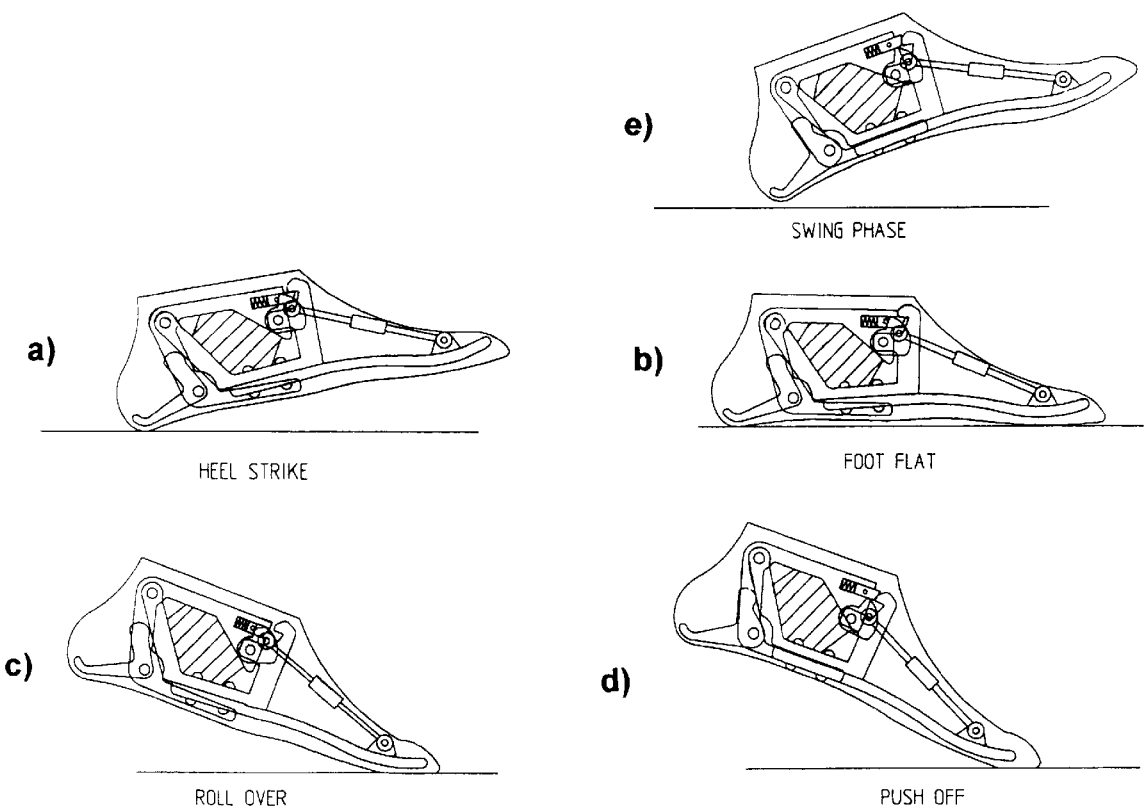
FIGS. 5a–5e show sectional view of such a prosthetic foot during a gait cycle.

The operation of the prosthetic foot is more clearly described with reference to FIG. 5.

In FIG. 5a the position of the parts of the foot 10 upon heel strike can be seen. At this point the force exerted on the heel lever 20 by the heel strike has compressed the energy storage means 14. The lock mechanism 16 is engaged, with the latch 36 in the cut-out 32 locking the chassis 22 and the storage lever 28 together, holding the elastomer buffer 26 in a compressed state. The normal heel cushioning and function of the foot 10 in this phase is controlled by the heel cushion 24 in a similar manner to, for instance a Sach foot, such that the foot 10 accommodates to the terrain and cushions the impact shock. This can be achieved without foot slap for individual amputees by balancing the action of the heel loading mechanism 12 against the stiffness of the heel cushion 24.

The energy thus stored in the elastomer buffer 26 is retained while the foot 10 is flat as can be seen in FIG. 5b. The toot 10 is pivoted rearwardly to a top plate (not shown) which also forms the ankle attachment. The ankle attachment can be pre-threaded and drilled to a standard Symes fixing or the European standard fitting for the Pyramid Alignment Device.

The roll-over phase is shown in FIG. 5c during which the toe-spring 18 is flexed by the pressure exerted by the leg with the result that the adjustable connecting rod 44, which is pivoted behind the effective toe joint centre, pushes the latch release cam 46 which in turn then pushes back the latch 38 via the protrusion 40. This then frees the energy storage lever 28.

The elastomer buffer 26 is then free to expand during push-off as shown in FIG. 5d and can provide extra lift for the leg on top of the foot through the movement of the main chassis 22.

The swing phase is shown in FIG. 5e during which the latch 38 is still released but the toe-spring 18 has now relaxed and therefore upon pressure being exerted upon the latch 38 is released. The latch 38 can then be pushed back inside the cutout 32 by a bevel 52 at the top of the U of the storage lever 28 upon heel strike.

The toe spring 18 may need to be produced in various sizes and stiffnesses. The heel cushion 24 and elastomer buffer 22 should have volumes to achieve maximum energy storage, and may need to be produced in several sizes to suit individual patient weights and activities.

Finally, the whole foot and ankle can be enclosed in a pre-moulded and sized foot cosmesis produced to fit standard sized shoes. The energy storing means 14 can be of various designs, such as, an elastomer rubber buffer, a gas filled strut, metal or composite coil spring or hydraulic or pneumatic cylinder.

The locking mechanism 16, however, could be actuated by a cam device operated by a servo electric motor with a microprocessor miniaturised electronic device to time the various phases of the walking cycle to unlock and release the energy at the appropriate time in the cycle. This could be preset and programmed by the Prosthetist during the trial fitting of the prosthesis to permit the development of a very advanced intelligent ankle and foot device.

I claim:

1. A prosthetic foot comprising a movable heel mechanism, an energy storage means acted on by the movable heel mechanism to store energy, during heel loading, and a control device attached to the energy storage means and to a release device so as to effect release of the stored energy to provide additional lift-off force during toe-off push-off.

2. A prosthetic foot according to claim 1, which further comprises a toe spring which acts as the release device.

3. A prosthetic foot according to claim 1, in which the energy release takes place at a specific event during a gait cycle.

4. A prosthetic foot according to claim 1, in which the control device controls the release of the energy by the energy storage means such that it is dependent upon one or more gait cycle variables.

5. A prosthetic foot according to claim 1, in which the control device can be externally adjusted.

6. A prosthetic foot according to claim 1, in which the control device controls the rate of release of the energy by external adjustment.

7. A prosthetic foot according to claim 1, in which the control device is an automatic clevis type locking mechanism.

8. A prosthetic foot according to claim 1, in which the energy storage means is an elastomer or rubber buffer.

9. A prosthetic foot according to claim 1, in which a predetermined proportion of the energy stored is released at a specific event between heel strike and toe-off.

* * * * *